United States Patent [19]

Paulik et al.

[11] 4,060,547
[45] * Nov. 29, 1977

[54] PRODUCTION OF DICARBOXYLIC ACIDS

[75] Inventors: Frank E. Paulik, Houston, Tex.; Arnold Hershman, Creve Coeur, Mo.; Walter R. Knox, Town and Country, Mo.; James F. Roth, Creve Coeur, Mo.

[73] Assignee: Monsanto Company, St. Louis, Mo.

[*] Notice: The portion of the term of this patent subsequent to Oct. 30, 1990, has been disclaimed.

[21] Appl. No.: 325,291

[22] Filed: Jan. 22, 1973

Related U.S. Application Data

[63] Continuation of Ser. No. 752,762, Aug. 15, 1968, abandoned, which is a continuation-in-part of Ser. No. 628,581, April 5, 1967, abandoned.

[51] Int. Cl.$^2$ ................... C07C 51/12; C07C 51/14
[52] U.S. Cl. ...................... 260/532; 260/515 P; 260/537 R; 560/204; 560/97
[58] Field of Search ........... 260/532, 533 AN, 514 K, 260/514 M, 537 R, 485 G

[56] References Cited

U.S. PATENT DOCUMENTS

| | | | |
|---|---|---|---|
| 2,739,169 | 3/1956 | Hagemeyer, Jr. | 260/533 AN |
| 3,020,314 | 2/1962 | Olderson | 260/533 AN |
| 3,065,242 | 11/1962 | Olderson et al. | 260/533 AN |
| 3,637,833 | 1/1972 | Fenton | 260/533 AN |
| 3,769,329 | 10/1973 | Paulik | 260/532 |
| 3,772,380 | 11/1973 | Paulik | 260/532 |

Primary Examiner—Vivian Garner
Attorney, Agent, or Firm—Paul L. Passley; Elizabeth F. Sporar

[57] ABSTRACT

The present invention relates to a process for the preparation of dicarboxylic acids, specifically by the reaction of non-vicinal glycols; halogen containing derivatives in which the OH radical of the glycol is substituted by Cl, Br, or I; ester derivatives of glycols; and cyclic ether derivatives of glycols; with carbon monoxide in the presence of catalyst compositions essentially comprising rhodium or iridium compounds and complexes, together with a halide promoter.

21 Claims, No Drawings

PRODUCTION OF DICARBOXYLIC ACIDS

This is a continuation, of application Ser. No. 752,762, filed Aug. 15, 1968, now abandoned, which was a continuation-in-part of appln. Ser. No. 628,581, filed Apr. 5, 1967, now abandoned.

This invention relates to a process for the preparation of dicarboxylic acids. More particularly, it relates to a process for the reaction of non-vicinal glycols, their halogen, ester and cyclic ether derivatives, with carbon monoxide in the presence of catalyst compositions essentially comprising rhodium or iridium compounds and complexes, to yield dicarboxylic acids selectively and efficiently.

Carbonylation processes for the preparation of carboxylic acids from alcohols, including glycols, are known in the art and have been directed especially to the production of adipic acid. The prior art teaches the use of a number of catalysts for the synthesis of carboxylic acids by reaction of alcohols with carbon monoxide at elevated temperatures and pressures in both gas phase, fixed bed reactions and liquid phase reactions. Catalysts such as phosphoric acid, phosphates, activated carbon, heavy metal salts such as zinc and cuprous chlorides, silicates of various metals, and boron trifluoride in various hydration states have been reported to function for the production of adipic acid by reaction of 1,4-butanediol or tetrahydrofuran, with carbon monoxide at elevated temperatures and pressures of the order of 300° C and 5,000 psig, respectively. However, even under such severe conditions the yields of acid were substantially poor, and therefore, uneconomical. Somewhat less severe reaction conditions of temperature and/or pressures have been reported in the literature employing specific catalyst compositions, e.g., 330° C–340° C and 2,250 psig using liquid phosphoric acid containing copper phosphate; 300° C–500° C and 2,000 psig–4,000 psig using active charcoal impregnated with phosphoric acid; and 260° C–360° C and 2,800 psig–15,000 psig using metal carbonyls, such as iron, cobalt and nickel, in conjunction with their halides or free halogens in the liquid phase. Even using these specific catalyst compositions at the less severe reaction conditions, substantially poorer yields of the desired dicarboxylic acid product and substantially slower reaction rates are obtained than those achieved in the process of this invention.

Certain disadvantages present in the carbonylation processes described in the prior art are catalyst instability, lack of product selectivity, and low levels of catalyst reactivity. One particular disadvantage of carbonylation processes of the prior art is their dependence upon the use of catalysts comprised of metal carbonyls or certain modified metal carbonyls including dicobalt octacarbonyl, iron carbonyl and nickel carbonyl, all of which require the use of high partial pressures of carbon monoxide to remain stable under the necessarily high reaction temperatures employed. For example, dicobalt octacarbonyl requires partial pressures of carbon monoxide as high as 3,000 psig to 10,000 psig under normal carbonylation conditions of 175° C to 300° C.

Still another disadvantage of carbonylation processes disclosed in the prior art is their relatively low level of activity. This low level of activity requires higher catalyst concentrations, longer reaction times, and higher temperatures to obtain substantial reaction rates and conversions. Consequently, larger and costlier processing equipment is required.

Another disadvantage of carbonylation processes disclosed heretofore is their inability to maintain high selectivity to the desired dicarboxylic acid at temperatures required for high conversion levels and high reaction rates. At these higher temperatures undesirable by-products comprising substantial amounts of ethers, lactones, aldehydes, higher dicarboxylic acids, carbon dioxide, methane and water are formed, thereby resulting in substantial yield losses and necessitating additional product purification and recycle steps in the processing.

Another disadvantage of carbonylation processes described in the prior art is their dependence on catalyst systems which require the use of substantially chemically pure carbon monoxide feedstocks to maintain high selectivity and high yield to the desired carboxylic acid product. For example, certain cobalt and nickel containing catalyst systems described heretofore when employed with carbon monoxide feed streams containing impurities such as hydrogen, result in the production of a number of undesirable by-products including methane, carbon dioxide, aldehydes, alcohols and glycols of the same carbon number as the desired dicarboxylic acid, and carboxylic acids of higher carbon number than desired. Consequently, substantial loss in selectivity and yield to the desired dicarboxylic acid occurs. Catalysts of the prior art cause the formation of troublesome gaseous by-products such as carbon dioxide and methane in the reactor system, thereby suppressing the carbon monoxide partial pressure and ultimately causing a decrease in the desired carbonylation reaction rate. Often additional processing steps are required to remove these undesirable by-products, necessitating the use of larger and costlier processing equipment.

It is, therefore, an object of the present invention to overcome the above disadvantages and thus provide an improved and more economically and commercially feasible carbonylation process for the production of dicarboxylic organic acids and their esters in liquid phase and vapor phase processes.

Another object of this invention is to provide a more reactive and more stable carbonylation catalyst composition than has been heretofore described in the prior art.

Still another object of the present invention is to provide a more selective and more reactive carbonylation catalyst composition for the production of dicarboxylic acids.

Another object of the present invention is to provide a carbonylation catalyst composition which results in the production of a higher yield of the desired dicarboxylic acid with no substantial formation of carbon dioxide, methane, water and other undesirable by-products.

The present invention constitutes an improved carbonylation process enabling the efficient and selective production of dicarboxylic acids by reaction of non-vicinal glycols; halogen containing derivatives in which the OH radical of the glycol is substituted by Cl, Br, or I; ester derivatives of glycols; and cyclic ether derivatives of glycols; with carbon monoxide in the presence of an improved and more stable catalyst, thus enabling the use of lower catalyst concentration, lower temperature, lower pressure, and shorter contact time than has been generally possible heretofore and facilitating product isolation, catalyst recovery and recycle without substantial catalyst decomposition and loss. The present catalyst may be employed using a solution of the catalyst (liquid phase operation), or a solid catalyst (vapor phase operation).

In accordance with a preferred embodiment of the present invention, non-vicinal glycols or derivatives having n carbon atoms are converted selectively to an acid having two more carbon atoms by reacting the glycol or derivative in the liquid phase with carbon monoxide at temperatures from about 125° C to 250° C and at partial pressures of carbon monoxide from 5 psig to 5,000 psig, preferably 75 psig to 1,000 psig, although higher pressure may be employed, in the presence of a catalyst system comprised of an active portion, for example, a rhodium or iridium component, and a promoter portion for example, a halogen and/or halogen compounds, preferably bromine or iodine.

The present process is particularly advantageous at lower pressures, although higher pressures may also be used.

As referred to above, for the preferred embodiment of the invention, the catalyst as charged to the reactor is a solution containing a preformed Rh or Ir component containing a halogen promoter and other moieties if desired. The catalyst essentially includes a Rh or Ir component containing a halogen promoter, as the active component, such as $[Rh(CO)_2I]_2$, $[(n-Bu)_4P][RH(CO)_2I_2]$, $[Ir(CO)_2Cl]_2$, $RhI_3$, $RhBr_3$, $[(C_6H_5)_3P]_2Rh(CO)I$, $[Rh(CO)_2Br]_2$, $[(C_6H_5)_3P]_2Rh(CO)(Cl)(CH_3I)$, $[(C_6H_5)_3As]_2Rh(CO)Br$, $IrCl_3 \cdot 3H_2O$, $Na_2IrCl_6$, $[(C_6H_5)_3AsCH_3][Rh(CO)_2(I)_2]$, etc. The halogen promoter portion of the present catalyst system may or may not be catalytically active in itself, but promotes the reaction in various ways, such as by facilitating cleavage of the carbon-oxygen bond in the alcohol, or by rendering the rhodium species less volatile than the unmodified rhodium carbonyl.

The active catalytic portion or first component of the preformed catalyst is prepared from rhodium or iridium species, e.g. rhodium metal, simple rhodium salts, organorhodium compounds, and coordination compounds of rhodium, specific examples of which may be taken from the following partial list of suitable rhodium or iridium precursors:

| | |
|---|---|
| Rh metal | $[(n-C_4H_9)N][Rh(CO)_2X_2]$ where $X = Cl^-$, $Br^-$, $I^-$ |
| $IrCl_3 \cdot 3H_2O$ | $[(n-C_4H_9)_4Rs]_2[Rh_2(CO)_2Y_4]$ where $Y = Br^-$, $I^-$ |
| $Na_2IrCl_6$ | $[(n-C_4H_9)_4P][Rh(CO)_4]$ |
| $RhI_3$ | $Rh[(C_6H_5)_3P]_2(CO)Br$ |
| $RhCl_3 \cdot 3H_2O$ | $Rh[(n-C_4H_9)_3P]_2(CO)Br$ |
| $RhBr_3 \cdot 3H_2O$ | $Rh[(n-C_4R_9)_3P]_2(CO)I$ |
| $Rh_2(CO)_4Cl_2$ | $RhBr[(C_6H_5)_3P]_3$ |
| $Rh_2(CO)_4Br_2$ | $RhI[(C_6H_5)_3P]_3$ |
| $Rh_2(CO)_4I_2$ | $RhCl[(C_6H_5)_3P]_3$ |
| $Ir(CO)Cl(P\phi_3)_2$ | $RhCl[(C_6H_5)_3P]_3H_2$ |
| $Rh[(C_6H_5)_3P]_2(CO)I$ | $[(C_6H_5)P]_3Rh(CO)H$ |
| $Rh[(C_6H_5)_3P]_2(CO)Cl$ | $Rh[(C_2H_4)_2Cl]_2$ |
| $RhCl[(C_6H_5)_3P]_2(CH_3I)_2$ | $K_4RH_2Cl_2(SnCl_3)_4$ |
| $Rh(SnCl_3)[(C_6H_5)_3P]_3$ | $K_4Rh_2Br_2(SnBr_3)_4$ |
| $RhCl(CO)[(C_6H_5)_3As]_2$ | $K_4Rh_3I_2(SnI_3)_4$ |
| $RhI(CO)[(C_6H_5)_3Sb]_2$ | $Rh_2O_3$ |
| $[Ir(CO)Cl]_2$ | $IrO_2$ |
| | $Rh(NO_3)_3$ |

The active catalytic portion or primary component of the catalyst system of this invention, as a solution, or as a supported solid catalyst, may exist as a coordination compound of rhodium or iridium, carbon monoxide, and a halide (X) such as chloride, bromide and iodide, $[Rh^{+1}(CO)_x(X)_y]$ where $x + y = 4$, including both neutral and ionic complexes, or a coordination compound, $[Rh^{+3}(CO)_x(X)_y(Z)_q]$ where $x + y + q = 5$ or 6, which includes other suitable ligands (Z), if desired, such as amine, organophosphine, organoarsine, and/or organostibine ligands, other ligands; e.g., hydride; alkyl, acyl and aryl (1–20 carbon atoms); and trihalostannate or any neutral, cationic, or anionic moiety necessary to satisfy the coordination number of the central metal atom, rhodium, and thus form a coordination compound or complex of rhodium as described above.

Preferred catalyst systems for the process of this invention are typically coordination complexes of rhodium, carbon monoxide and iodine such as $[Rh(CO)_2I_2]^-$, $[Rh(CO)I_4]^-$, or $[Rh(CO)_2I]_2$.

The term coordination compound or coordination complex used throughout this specification means a compound or complex formed by combination of one or more electronically rich molecules or atoms capable of independent existence with one or more electronically poor molecules or atoms, each of which may also be capable of independent existence.

The promoting portion or second component of the catalyst system consists of a halogen and may be supplied as a halogen compound such as hydrogen halide, alkyl- or aryl-halide, metal halide, ammonium, phosphonium, arsonium, stibonium halide, etc., and may be the same or different from any halogen component already present in the precursor Rh or Ir component of the catalyst system. Halogen or halide compounds are suitable for the promoter portion of the catalyst, but those containing iodine and bromine are preferred, with hydrogen iodide constituting a more preferred member. Accordingly, suitable compounds providing the promoter portion of the catalyst system of this invention may be selected from the following list of preferred halogen and/or halogen containing compounds:

| | | |
|---|---|---|
| $RX_n$ where (n is 1 to 3 and | R = any alkyl-, alkylene- or aryl-group X = Cl, Br, or I | e.g., $CH_3I$, $C_6H_5Br$, $CH_3CH_2I$, $ICH_2CH_2I$, etc. |
| $X_2$ or $X_3^-$ where | X = Cl, Br, or I | e.g., $Br_2$, $I_2$, $I_3^-$, etc. |
| HX where | X = Cl, Br, or I | e.g., HBr, HI |
| RCX where ‖ O | R = any alkyl- or aryl-group | e.g., $CH_3CI$, etc. ‖ O |
| and $R_4MX$, $R_4MX_3$, or $R_3MX_2$ where | X = Cl, Br, or I R = hydrogen or any alkyl- or aryl-group M = N, P, As or Sb X = Cl, Br or I | e.g., $NH_4I$, $PH_4I_3$, $PH_3I_2$, $PH_3Br_2$, $(C_6H_5)_3PI_2$, and/or combinations of R, M and X |

The promoter portion or second component of the catalyst may alternatively be charged to the reactor separately from the active catalyst or first component, or it may be incorporated into the active component, e.g., $RhI[(C_6H_5)_3P]_3$. The rhodium compound or first component of the catalyst system may be prepared prior to charging the reactor or generated in situ. Subsequently, after the first component is in the reactor and dissolved in a suitable solvent, the promoter or second component of the catalyst may be added as a solid or liquid compound or in solution in a suitable solvent compatible with that already employed in the process of this invention. However, the promotor portion of the catalyst may also be incorporated in the active catalyst or first component either during the preforming or during the in situ generation of the metal complex.

The preparation of the active catalyst complex which includes both rhodium and halogen promoter components may be accomplished by a variety of methods. However, it is thought that a substantial part of the precursor rhodium component is converted to the monovalent state during the preparative treatment. In general in the process of this invention, it is preferable to preform the active carbonylation catalyst system which contains both rhodium and halogen promoter components. For example, to prepare the catalyst system, the first component of the catalyst system, e.g., finely divided rhodium metal (powder), a simple rhodium salt or rhodium compound as a precursor is dissolved in a suitable medium, and carbon monoxide is bubbled through the above rhodium solution, preferably while maintaining gentle heating and stirring of the rhodium solution. Then an acidic solution of the desired halogen promoter is added to form an active catalyst solution containing the necessary rhodium and halogen promoter components.

Generally, any preformed rhodium compound may be charged to the reactor directly and, if desired, is dissolved in an appropriate solvent. If desired, the rhodium coordination compounds described above may be prepared from any of the simpler types of rhodium salts. For example, to prepare the catalyst system, the first component of the catalyst system, e.g., a rhodium salt such as $RhCl_3.3H_2O$ is dissolved in a suitable solvent such as ethanol. Subsequently, carbon monoxide is bubbled through the solution where an intermediate, such as the dimer $[Rh(CO)_2Cl]_2$, is produced wherein the rhodium is in the monovalent state. The second or promoter component is, for example, added to the above solution, e.g., as aqueous HI, or methyl iodide or other halogen containing compound. As another embodiment, the rhodium precursor, e.g., $RhCl_3.3H_2O$ or $Rh_2O_3.5H_2O$, may be dissolved in a dilute aqueous acid solution, e.g., HCl, acetic acid, etc., as solvent. Then the solution of the rhodium compound is heated, for example, to 60° C–80° C, or in general at a temperature below the boiling point of the solvent, with stirring. A reducing agent such as carbon monoxide is bubbled through the said solution to obtain the rhodium component at least in part in the monovalent state. The halogen promoter is added as described herein, although the halogen promoter may also be added first.

Still another embodiment of the present invention employs compounds of monovalent rhodium initially, wherein the transformation to active catalyst does not involve a change of valence. For example, monovalent rhodium salts such as $Rh[(C_6H_5)_3P]_3Cl$, $[Rh(C_6H_5)_3P]_2(CO)Cl$, $[Rh(C_6H_5)_3P]_3H$ are dissolved in a suitable solvent and carbon monoxide is subsequently passed through a solution that is preferably warmed and stirred. Subsequent addition of an acidic solution of the halogen promoter, e.g., methyl iodide, methyl bromide, aqueous HI, HBR, etc., results in formation of an active carbonylation catalyst solution containing the necessary rhodium and halogen components.

Alternate embodiments of the present invention include the use of other rhodium components in various oxidation states, e.g., rhodium metal (zero valence state), rhodium salts, e.g., $RhI_3$ (+3 valence state), other rhodium compounds, e.g., tris-acetylacetonato rhodium (III) (+3 valence state) etc.; with suitable chemical reagents to accomplish the desired transformation to the monovalent rhodium state. Such reagents include reducing agents, e.g., hydrogen, carbon monoxide, hydrazine, formic acid, phenylhydrazine, etc.; and oxidizing agents, e.g., elemental halogens ($I_2$ or $Br_2$), mineral acids, (HCl, HBr, $HNO_3$, HI), peroxides ($H_2O_2$, cumene hydroperoxide, etc.).

This catalytic solution containing the necessary rhodium and halide components is then ready for use as discussed above. Often it may be beneficial and desirable to have the concentration of the second component or promoter portion of the catalyst system, for example, iodide such as HI or $CH_3I$, in excess of that required to form a stoichiometric compound such as described above. In the same way the two components, e.g., a rhodium compound and an iodine or bromine component are provided in a single molecule by beginning with rhodium triiodide or rhodium tribromide as the catalyst precursor for the reaction of an alcohol with carbon monoxide to produce an organic acid. The present discussion is based upon the catalyst precursors as charged. The ultimate nature of the catalyst as modified by reaction conditions, and the presence of promoters and reactants, has not been completely elucidated. However, it has been found that the use of the components described herein provides a highly superior catalyst and process for the production of dicarboxylic acids.

Although any ratio of promoter portion or second component of the catalyst system may be employed, ratios of promoter portion to active portion expressed as atoms of halogen in the promoter portion to atoms of rhodium in the active portion of the catalytic system in the range of 1:1 to 2500:1 are generally employed. However, the preferred range is 3:1 to 300:1 halogen atoms per rhodium atom.

The liquid reaction medium employed may be any solvent compatible with the catalyst system and may include pure polyhydric alcohols, or mixtures of the alcohol feedstock and/or the desired carboxylic acid and/or esters of these two compounds or other carboxylic acids such as acetic acid. The preferred solvent and liquid reaction medium for the process of this invention is a monocarboxylic acid having 2–6 carbon atoms, e.g., acetic, propionic, butyric, pentanoic, and hexanoic acids, including isomeric forms. Water may also be added to the reaction mixture to exert a beneficial effect upon the reaction rate. Other liquid phase reaction media may be chosen such as the organophosphorus ligands, e.g., triphenylphosphite.

Suitable feedstocks are non-vicinal glycols and their derivatives, although the glycol feed may be charged together with an acid or ester as discussed below. Preferred glycols have two carbon atoms less than the desired dicarboxylic acid product. These feedstocks also include halide, ester, and cyclic ether derivatives of the desired glycol feedstock, for example, tetrahydrofuran; 1,4-dibromobutane; 1,6-diiodohexane; 1,4-butaneglycol diacetate; 1,3-dibromobutane; 1,4-dichlorobutane; paradiiodobenzene; 1,5-dichlorooctane. Ester derivatives are based upon the glycol and a carboxylic acid of 1–20 carbon atoms, e.g., 3–20 carbon atoms in the glycol moiety and 1–20 carbon atoms in the acid moiety.

Examples of preferred feedstocks include the group of non-vicinal aliphatic glycols having 3 to 20 carbon atoms, and aromatic glycols having from 6 to 20 carbon atoms incuding resorcinol or hydroquinone to yield phthalic acids, and also 1,4-butanediol, which when subjected to reaction with carbon monoxide under the conditions described herein with the catalyst of the invention, yields adipic acid. However, if adipic acid is the desired product, the feedstock may consist not only of 1,4-butanediol, but also derivatives thereof, such as 1,4-dibromobutane, tetrahydrofuran and/or combinations of these.

In accordance with the present invention, the carbonylation reaction may be carried out by intimately contacting a nonvicinal glycol or derivatives, which depending on the carbon number and operating conditions may either be in the vapor or liquid phase, with gaseous carbon monoxide in a liquid phase containing the catalyst system prepared from $RhCl_3.3H_2O$ or other rhodium precursor. The reaction is conducted in the presence of halogen containing promoters, such as hydrogen iodide, under conditions of temperature and pressure suitable, as described herein, to form the carbonylation product. The particular conditions selected are the same whether the glycol, halogen, or ether derivative is charged as a vapor or liquid. The temperature accordingly will be in the range of 125° C to 250° C with the preferred range being 165° C to 225° C. Partial pressures of carbon monoxide of the order of 5 psig to 5,000 psig may be employed; however, 75 psig to 1,000 psig carbon monoxide partial pressure is generally preferred. Higher pressures may be used if desired under appropriate conditions.

Alternatively, dicarboxylic acids may be produced if desired via reaction of non-vicinal glycols, their halogen or ether derivatives, together with carbon monoxide in the vapor phase over the rhodium containing catalyst systems described above, dispersed upon inert supports. Such a catalyst system may be operated as a conventional fixed bed catalystic reactor. For example, tetrahydrofuran, hydrogen iodide, and carbon monoxide may be passed over a catalyst system consisting, for example, of $[Rh(CO)_2Cl]_2$ dispersed on an inert support material such as alundum, activated carbon, clays, alumina, silica-alumina, and ceramics, etc., in a fixed bed reactor maintained at elevated temperature and pressure, as described above, to produce adipic acid in high yields. However, use of a liquid reaction medium is preferred in the process of this invention using dissolved or dispersed active catalytic and promoter components.

A typical carbonylation reaction selective to dicarboxylic acid requires at least two of carbon monoxide per mole of alcohol or ether. Excess of carbon monoxide over the aforesaid stoichiometric amount, however, may be present. Carbon monoxide streams containing inert impurities such as hydrogen, carbon dioxide, methane, nitrogen, noble gases, water and paraffinio hydrocarbons having from 1 to 4 carbon atoms, may be employed, if desired, for example, from an available gas stream, with no ill effect; however, in such cases total reactor pressure will have to be increased to maintain a desired carbon monoxide partial pressure. The concentration of carbon monoxide in the feed gas mixture is from 1 vol. % to 99.9 vol. %, a preferred range being from 10 vol. % to 99.9 vol.%

The reaction rate is dependent upon catalyst concentration and temperature. Concentrations of the rhodium compound or the first component of the catalyst system in the liquid phase, between $10^{-6}$ moles/liter and $10^{-1}$ moles/liter, are normally employed, with the preferred range being $10^{-4}$ moles/liter to $10^{-2}$ mole/liter. Higher concentrations even to the extent of 1 mole/liter may, however, be used if desired. Higher temperatures also favor higher reaction rates.

The concentration of the second component or promoter portion of the catalyst system may vary widely over the broad concentration range of $10^{-8}$ moles/liter to 18 moles/liter, based on halogen atom. In the process of this invention, however, the preferred concentration range of promoter is $10^{-4}$ moles/liter to 2 moles/liter of catalyst solution.

The active rhodium catalytic component is preferably supplied as a catalyst solution. The solution can also include liquid reactants, products and mixtures thereof which function as solvents or reaction media.

When glycol ester or half-ester is present in the feedstock, it is normally charged with equimolar amounts of water, although more or less water may be used. The use of the ester is on the basis that a molar quantity of water is present equivalent to the number of moles of ester present. It has been found that water generally exerts a beneficial effect on the rate of reaction. However, adding water, with the feed in excess of the equimolar quantity, e.g., an excess of 50% to 300% of such equimolar quantity, already present with ester, as discussed above, promotes the production of dicarboxylic acid.

The rhodium catalysts of the present invention are characterized by a high degree of specificity for the carbonylation reaction, e.g., the reaction of alcohol groups with carbon monoxide to obtain carboxylic acids. Such control over the various competing reactions to obtain the carboxylic acid in high yield is surprising since other metal catalysts do not show such specificity. The iron group metals such as iron, cobalt and nickel differ from the present rhodium catalysts in that the iron group metals simultaneously catalyze hydrogenation reactions to a very high degree. Furthermore, the iron group catalysts, particularly cobalt and nickel, require a far higher carbon monoxide partial pressure to remain stable. When moderate pressures, e.g., less than about 2,000 psig carbon monoxide partial pressure are employed, at a temperature of 175° C, the cobalt catalyst is found to plate out or decompose to the free metal which plates on the walls of the reactor and is thus lost as a catalyst.

Another distinction of the rhodium catalysts over the cobalt catalysts is the elimination of undesirable gaseous by-products, including carbon dioxide and methane which are obtained as a result of the water-gas shift reaction which is strongly catalyzed by cobalt.

The discussion herein relating to production of carboxylic products includes production of derivatives, such as esters, by reaction of the desired carboxylic acid with an alcohol moiety which may be the same or different from the feedstock, and is carried out in situ in the reactor by control of alcohol conversion, or accomplished separately by subsequent reaction in a separate vessel.

For a better understanding of the process of the present invention specific embodiments of the process are presented below. These examples and illustrations are not to be construed in any way as limiting the scope of the invention.

EXAMPLE 1

A batch reactor is charged with the following ingredients: 0.396 grams of a rhodium compound having the formula $RhCl_3.3H_2O$, 51 grams of a promoter consisting of aqueous 57 wt. % hydriodic acid, 196.9 grams of acetic acid as a solvent, and 100 grams of 1,4-butanediol as feedstock.

The reactor is pressurized with carbon monoxide to a total pressure of 1,000 psig, corresponding to a carbon monoxide partial pressure of about 800 psig, at the reaction temperature of 200° C. The reaction is carried out at constant pressure. The reaction products are subsequently analyzed by gas chromatographic techniques.

The selectivity to the formation of the desired dicarboxylic acid product, adipic acid, is greater than 38 mol %. No substantial amounts of by-products such as aldehydes, higher boiling carboxylic acids, methane, or carbon dioxide are formed.

When this experiment is conducted with the equivalent molar quantity of cobalt chloride instead of rhodium chloride as the catalyst, the selectivity and yield of the desired acid product are decreased significantly. It has been found that cobalt catalysts also cause hydrogenation reactions such as hydrogenation of the desired carboxylic acid product to aldehydes and alcohols of the same number of carbon atoms. Consequently, the use of cobalt catalysts results in the substantial production of various undesirable by-products including higher carbon number alcohols, carboxylic acids, and derivatives.

Still another distinction of the rhodium catalysts compared to the cobalt and nickel catalysts is the fact that significantly lower carbon monoxide partial pressure can be used without encountering catalyst decomposition.

EXAMPLES 2-12

The procedure of Example 1 is also followed in detailed Examples 2-12, in order to illustrate the variation of parameters. Data of these runs are shown in the accompanying table, including variation of catalyst components, feedstock, and reaction conditions along with results for product selectivity.

EXAMPLE 13

A solid supported catalyst containing an iridium component and a halogen promoter dispersed upon an inert support is prepared in the following manner: An amount of 0.6 g. of an iridium compound, having the formula $IrCl_3.3H_2O$, is dissolved in 2-methoxy ethanol. The solution is warmed to 60° C, and carbon monoxide is bubbled through the solution until a pale yellow color is obtained indicating the presence of the monovalent complex. Then the solution is cooled and 20 ml of 57 wt. % hydriodic acid is added to the solution of the iridium compound. Subsequently, the resulting solution is added to 20 ml of an activated carbon (Pittsburgh Activated Carbon Co.). The excess solvent is evaporated using a rotary evaporator under vacuum. The resulting catalyst is vacuum dried at 60° C for about 16 hours. The catalyst is then preheated in nitrogen at 200° C for one hour.

Ten (10) ml of the above supported catalyst is charged into an 18-inch Pyrex glass vertical reactor 30 mm in diameter. The resulting catalyst bed, 2 cm in depth, is covered with 100 ml of inert packing as a preheater. Gaseous tetrahydrofuran is supplied to the reactor in a nitrogen diluent stream and is subsequently converted to adipic acid at high selectivity. The process is conducted at a feed rate (moles per hour) of tetrahydrofuran, 0.14; HI, 0.02; water, 0.28; and CO, 0.54. The pressure at which the gaseous reactants contact the supported catalyst is 500 psig, corresponding to a carbon monoxide partial pressure of about 125 psig at a reaction temperature of 175° C.

The gaseous reactor effluent contains the desired dicarboxylic acid product, adipic acid, and unreacted tetrahydrofuran, water, carbon monoxide and promoter. When this example is repeated except that hydrogen gas is used as the diluent gas in the feedstream, similar results are obtained.

Table

Run Conditions: [Rh or Ir]× $10^{-3}$ M; [Br or I] 0.6 M; 50 ml solvent; Time: 17 hours

| Ex. | Feedstock | Catalyst Precursor Rh | Promoter | Solvent | Temp. °C | Reactor Press. psig | Major Product Selectivity (mol %) |
|---|---|---|---|---|---|---|---|
| 2 | $HO(CH_2)_3OH$ | $RhCl_3.3H_2O$ | HI | $CH_3COOH$ | 200 | 1,000 | $HOOC(CH_2)_3COOH$ (30) |
| 3 | $HO(CH_2)_4OH$ | $Rh(P\phi_3)_2COCl$ | $CH_3I$ | $CH_3COOH$ | 175 | 700 | $HOOC(CH_2)_4COOH$ (74) |
| 4 | $HO(CH_2)_4OH$ | $Rh(P\phi_3)_3Cl$ | $CH_3I$ | $CH_3COOH$ | 215 | 1,100 | $HOOC(CH_2)_4COOH$ (22) |
| 5 | $HO(CH_2)_8OH$ | $Rh(P\phi_3)_2(CO)Cl$ | $CH_3I$ | $CH_3CH_2COOH$ | 200 | 1,000 | $HOOC(CH_2)_8COOH$ (31) |
| 6 | tetrahydrofuran | $RhCl_3.3H_2O$ | HI | $CH_3COOH$ | 175 | 700 | $HOOC(CH_2)_4COOH$ (14) / $HOOC(CH_2)_3COOH$ (38) |
| 7 | tetrahydrofuran | $[Rh(CO)_2Cl]_2$ | HBr | $H_2O$ | 175 | 325 | $HOOC(CH_2)_4COOH$ (5) |
| 8 | $HO(CH_2)_2CH(OH)CH_3$ | $RhI_3$ | $CaI_2.3H_2O$ | $H_2O$ | 200 | 1,000 | $HOOC(CH_2)_2CHCOOH$ (25), $CH_3$ |
| 9 | catechol (OH, OH) | $[Rh(CO)_2Br]_2$ | HBr | $CH_3CH_2COOH$ | 215 | 1,100 | HOOC—⟨benzene⟩—COOH (1.4) |
| 10 | diiodobenzene (I, I) | $Rh(NO_3)_3.2H_2O$ | HI | $CH_3COOH$ | 200 | 1,000 | HOOC—⟨benzene⟩—COOH (5) |
| 11 | $HOCH_2$—$CHCH_3$, OH | $RhCl_3.3H_2O$ | HI | $CH_3COOH$ | 200 | 1,000 | No dibasic acids |
| 12 | $HO(CH_2)_4OH$ | $Ir(CO)Cl(P\phi_3)_2$ | HI | $CH_3COOH$ | 175 | 700 | $HOOC(CH_2)_4COOH$ (69) |

What is claimed is:

1. A process for the carbonylation of reactants selected from the group consisting of tetrahydrofuran and non-vicinal acyclic glycols wherein the hydroxyl groups are on different carbon atoms and there are from 3 to 20 carbon atoms in the glycol, said process comprising contacting 1. at least one of said reactants,
2. carbon monoxide, and
3. a catalyst system consisting essentially of
   a. a metal compound selected from the group consisting of rhodium compounds, and iridium compounds and
   b. a halogen component which is bromine, iodine, a bromide compound or an iodide compound, wherein during said contacting, said metal compound and said halogen component are present in an amount sufficient to catalyze the carbonylation of said reactants, said contacting being carried out at a temperature in the range of 125° C to 250° C.

2. The process of claim 1 wherein said metal compound of 3(a) is dispersed upon an inert solid support.

3. The process of claim 2 wherein at least one of said reactants is 1,4-butanediol.

4. The process of claim 2 wherein said carbonylation is carried out in the vapor phase.

5. The process of claim 4 wherein said metal compound of 3(a) is an iridium compound.

6. The process of claim 4 wherein said metal compound of 3(a) is a rhodium compound.

7. The process of claim 1 wherein said contacting is also in the presence of water.

8. The process of claim 7 wherein at least a portion of said halogen component of 3(b) is provided by hydrogen iodide, hydrogen bromide, methyl iodide or methyl bromide.

9. The process of claim 7 wherein said metal compound of 3(a) is provided by a material selected from the group consisting of iridium salts, rhodium salts, iridium oxides, rhodium oxides, iridium carbonyls consisting only of iridium and carbonyl moieties and rhodium carbonyls consisting only of rhodium and carbonyl moieties.

10. The process of claim 7 wherein at least one of said reactants is 1,4-butanediol.

11. The process of claim 7 wherein said halogen component of 3(b) is provided by iodine or an iodide compound and said iodine or iodide compound is present in an amount such as to produce an iodine to iridium or an iodine to rhodium atomic ratio in the range of 1:1 to 2500:1.

12. The process of claim 11 wherein said metal compound of 3(a) is dispersed upon an inert solid support.

13. The process of claim 12 wherein said carbonylation is carried out with said reactants in the vapor phase.

14. The process of claim 7 wherein said metal compound of 3(a) and said halogen component of 3(b) are present in a liquid reaction medium.

15. The process of claim 14 wherein said metal compound of 3(a) is an iridium compound.

16. The process of claim 15 wherein the halogen component of 3(b) is present in an amount of from 1:1 to 2500:1 atoms of halogen per atom of iridium.

17. The process of claim 16 wherein said halogen component of 3(b) is iodine or an iodide compound.

18. The process of claim 14 wherein said metal compound of 3(a) is a rhodium compound.

19. The process of claim 18 wherein the halogen component 3(b) is present in an amount of from 1:1 to 2500:1 atoms of halogen per atom of rhodium.

20. The process of claim 19 wherein said halogen component of 3(b) is iodine or an iodide compound.

21. The process of claim 20 wherein at least one of said reactants is 1,4-butanediol.

* * * * *